(12) United States Patent
Miyazawa et al.

(10) Patent No.: US 7,173,147 B2
(45) Date of Patent: Feb. 6, 2007

(54) PROCESS FOR PRODUCING ACRYLIC ESTER COMPOUND

(75) Inventors: Satoru Miyazawa, Kawagoe (JP); Yusuke Kuramoto, Kawagoe (JP); Satoru Kobayashi, Kawagoe (JP); Kazuhiko Maeda, Kawagoe (JP)

(73) Assignee: Central Glass Company Limited, Ube (JP)

( * ) Notice: Subject to any disclaimer, the term of this patent is extended or adjusted under 35 U.S.C. 154(b) by 268 days.

(21) Appl. No.: 10/995,334

(22) Filed: Nov. 24, 2004

(65) Prior Publication Data
US 2005/0171375 A1    Aug. 4, 2005

(30) Foreign Application Priority Data
Nov. 27, 2003    (JP)    ............... 2003-396476

(51) Int. Cl.
C07C 233/00    (2006.01)

(52) U.S. Cl. .................. 560/223; 560/219; 560/220; 560/221

(58) Field of Classification Search ............... 560/219, 560/220, 221, 223
See application file for complete search history.

(56) References Cited

FOREIGN PATENT DOCUMENTS

EP    0824096 A2 *    7/1997

OTHER PUBLICATIONS

Jikken Kagaku Koza 19 "Syntheses of Organic Compounts", pp. 470-483, published 1957 by Maruzen Co.

* cited by examiner

*Primary Examiner*—J. Parsa
(74) *Attorney, Agent, or Firm*—Crowell & Moring LLP

(57) ABSTRACT

A process for producing an acrylic ester compound includes reacting in the presence of alkene an alcohol represented by the formula (1),

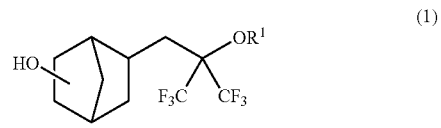

(1)

wherein $R^1$ represents a hydrogen atom, a fluorine atom, a straight-chain or branched hydrocarbon group, a fluorine-containing alkyl group, or an aromatic or aliphatic ring and optionally contains oxygen, sulfur or a carbonyl bond, with an acid halide represented by the formula (2),

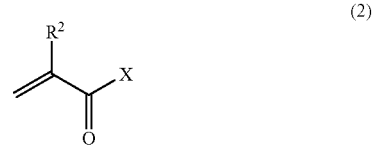

(2)

wherein $R^2$ represents a hydrogen atom, a halogen atom, a hydrocarbon group, or a fluorine-containing alkyl group, and X represents a halogen atom.

15 Claims, No Drawings

PROCESS FOR PRODUCING ACRYLIC ESTER COMPOUND

BACKGROUND OF THE INVENTION

The present invention relates to a process of producing an acrylic ester compound that is a polymerizable monomer useful for producing photoresists of vacuum ultraviolet region.

As typical examples of esterification, there have been known (a) a dehydration and condensation reaction between an alcohol and a carboxylic acid (see page 471 of a book, Jikken Kagaku Koza 19 "Syntheses of Organic Compounds" written in Japanese and published in 1957 by Maruzen Co.), (b) a transesterification reaction between an alcohol and a carboxylic ester (see page 478 of this book), and (c) a condensation reaction between an alcohol and a carboxylic halide in a basic condition (see page 476 of this book). In general, dehydration reactions and transesterification reactions are equilibrium reactions. Therefore, it is possible to achieve a high yield by using an alcohol in an excessive amount relative to that of a carboxylic acid or carboxylic ester. These two reactions, however, are not suitable for a large-scale production in case that the alcohol is complicated in structure and high in price.

On the other hand, the above condensation reaction proceeds even if the starting materials are reacted in a molar ratio of 1:1. Therefore, this reaction can be used for a large-scale production, even if the alcohol is high in price. This reaction, however, produces an acid (HX). Thus, it is generally known to trap this acid by adding an amine to the reaction system. This addition produces an amine halide salt, which must be removed by filtration and acid washing. Thus, the condensation reaction makes the operation cumbersome.

SUMMARY OF THE INVENTION

It is an object of the present invention to provide a process for producing an acrylic ester compound with high conversion and high yield without necessity of excessively using an alcohol as the raw material.

According to the present invention, there is provided a process for producing an acrylic ester compound. This process includes reacting in the presence of alkene an alcohol represented by the formula (1),

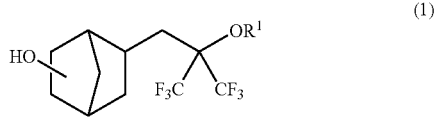

(1)

wherein $R^1$ represents a hydrogen atom, a fluorine atom, a straight-chain or branched hydrocarbon group, a fluorine-containing alkyl group, or an aromatic or aliphatic ring and optionally contains oxygen, sulfur or a carbonyl bond, with an acid halide represented by the formula (2),

(2)

wherein $R^2$ represents a hydrogen atom, a halogen atom, a hydrocarbon group, or a fluorine-containing alkyl group, and X represents a halogen atom.

DETAILED DESCRIPTION

If the alcohol represented by the formula (1) wherein $R^1$ represents a hydrogen atom is used in the above-mentioned conventional condensation reaction, the resulting acrylic ester compound is incorporated into the amine halide salt, since the acrylic ester compound is hydrophilic due to its terminal alcohol (—OH). Thus, the extraction operation for isolating the acrylic ester compound is cumbersome. As a result, the crude product recovery becomes very low.

In case that the condensation reaction is conducted without adding an amine, there occurs a by-product, that is, a compound in which an acid (HX) has been added to the carbon-carbon double bond of the acrylic ester compound. With this, conversion of the target acrylic ester compound becomes low.

The present inventors have unexpectedly found that the target acrylic ester compound can be efficiently obtained with high conversion and high yield by using an alkene as an acid (HX where X is a halide) trapping agent in a condensation reaction between the alcohol represented by the formula (1) and the acid halide represented by the formula (2). In other words, the alkene can trap an acid (HX) released by this condensation reaction.

As stated above, $R^1$ of the formula (1) represents a hydrogen atom, a fluorine atom, a straight-chain or branched hydrocarbon group, a fluorine-containing alkyl group, or an aromatic or aliphatic ring. $R^1$ optionally contains oxygen, sulfur or a carbonyl bond. The structure of $R^1$ is not particularly limited. The hydrocarbon group is preferably a $C_1$–$C_{20}$ hydrocarbon group optionally having a ring structure, such as methyl group, ethyl group, isopropyl group, cyclopentyl group, cyclohexyl group, norbornel group, adamantyl group, and benzyl group. $R^1$ with oxygen may be an acyclic ether group (e.g., methoxymethyl ether and methoxyethoxymethyl ether) or a cyclic ether group (e.g., tetrahydrofuran and tetrahydropyran). An example of the aromatic ring may be 4-methoxybenzyl group. $R^1$ with carbonyl group may be selected from acetyl group, pivaloyl group, tert-butoxycarbonyl group, and benzoyl group. $R^1$ is preferably a hydrogen atom, since $OR^1$ becomes a hydroxyl group For example, in case that the hydroxyl group is positioned at C5 or C6 of the norbornel ring in the formula (1), the relative steric configurations of the alkyl group at C2 of the norbornel ring and the hydroxyl group are not limited at all. It is possible to use a single stereoisomer or a mixture of at least two stereoisomers in terms of such steric configurations.

As stated above, $R^2$ of the formula (2) represents a hydrogen atom, a halogen atom, a hydrocarbon group, or a fluorine-containing alkyl group. Examples of the halogen atom include fluorine, chlorine and bromine. Examples of the hydrocarbon group include methyl group, ethyl group, propyl group, isopropyl group, butyl group, isobutyl group, sec-butyl group, tert-butyl group, cyclopentyl group, cyclohexyl group, phenyl group, benzyl group, and phenethyl group. Examples of the fluorine-containing alkyl group include those in which hydrogen atoms of the above-exemplified alkyl groups have been partially or totally replaced with fluorine atoms. The carbon atom number of the hydrocarbon group or fluorine-containing alkyl group may be from 1 to 20, preferably 1 to 4 from the viewpoint of polymerizability. $R^2$ is particularly preferably a hydrogen atom, fluorine atom or methyl group. Specific examples of the fluorine-containing alkyl group include trifluoromethyl group (—CF$_3$), trifluoroethyl group (—CH$_2$CF$_3$), and 1,1,1,3,3,3-hexafluoroisopropyl group (—CH(CF$_3$)$_2$), and its structure can be used without limitation. X of the formula (2) represents a halogen atom such as chlorine, bromine, and iodine. Of these, chlorine is preferable in terms of economy.

The amount of the acid halide is preferably 1 to 5 equivalents, more preferably 1 to 2 equivalents, per equivalent of the alcohol. If the acid halide is less than 1 equivalent, selectivity of the reaction may become too low. An amount greater than 5 equivalents is not preferable from the economical viewpoint.

The alkene can be used without particular limitation, as long as it is a hydrocarbon group. It may have a straight-chain, branched or ring structure. A conjugated diene (e.g., isoprene and cyclopentadiene) is not preferable as the alkene, due to the occurrence of a competitive reaction of a conjugated diene with the acid halide (reactant) or the acrylic ester compound (product). In other words, this competitive reaction may interfere with the acid (HX) trapping of the alkene. Examples of the alkene include ethylene, propylene, 1-butene, 2-butene, isobutene, 1-pentene, 2-pentene, 2-methyl-1-butene, 2-methyl-2-butene, 3-methyl-1-butene, methylenecyclobutane, 1,4-pentadiene, cyclopentene, 1-hexene, 2-hexene, 3-hexene, 2,3-dimethyl-1-butene, 2,3-dimethyl-2-butene, 3,3-dimethyl-1-butene, 2-ethyl-1-butene, 2-methyl-1-pentene, 2-methyl-2-pentene, 3-methyl-1-pentene, 3-methyl-2-pentene, 4-methyl-1-pentene, 4-methyl-2-pentene, 1,4-hexadiene, 1,5-hexadiene, 1-methyl-1-cyclopentene, 2-methyl-1,4-pentadiene, cyclohexene, 1-heptene, 2-heptene, 3-heptene, 4,4-dimethyl-1-pentene, 3-ethyl-2-pentene, 2-methyl-1-hexene, 2,3,3-trimethyl-1-butene, cycloheptene, vinylcyclohexane, 1-methyl-1-cyclohexene, methylenecyclohexane, norbornene, 2-methyl-1-heptene, 2-methyl-2-heptene, 1-octene, 2-octene, 3-octene, 4-octene, 2,3,4-trimethyl-2-pentene, 2,4,4-trimethyl-1-pentene, 2,4,4-trimethyl-2-pentene, cyclooctene, 1-nonene, 2-nonene, 3-nonene, and 4-nonene. It is optional to use a mixture of at least two of these. Preferable examples of the alkene include isobutene, 2-methyl-2-butene, 2-methyl-2-pentene, 1-methyl-1-cyclopentene, cyclohexene, 1-methyl-1-cyclohexene, methylenecyclohexane, and norbornene.

The amount of the alkene used may be 0.1 to 50 equivalents, preferably 0.5 to 20 equivalents, more preferably 1 to 10 equivalents, per equivalent of the alcohol. If the alkene is less than 0.1 equivalents, conversion may become too low due to the addition of the acid HX (generated by the condensation reaction) to the unsaturated bond of the acid halide (reactant) or acrylic ester compound (reaction product). An amount greater than 50 equivalents is not preferable from the economical viewpoint.

A solvent can be used without particular limitation as long as it is inert in the reaction. Preferable examples of the solvent include aromatic compounds (e.g., benzene, toluene, xylene, mesitylene, and trifluoromethylbenzene), aliphatic compounds (e.g., hexane, cyclohexane, heptane, and trifluoromethylcyclohexane), ethers (e.g., methyl-tert-butyl ether, diethyl ether, diisopropyl ether, tetrahydrofuran (THF), tetrahydropyran, and 1,4-dioxane), and halogen-containing compounds (e.g., methylene chloride, chloroform, and carbon tetrachloride). The reaction can proceed without using solvent. It is, however, optional to use a single solvent or a mixture of solvents in order to make the reaction proceed smoothly, while suppressing a polymerization reaction of the acid halide (reactant) or acrylic ester compound (reaction product). The solvent may be used in an amount of 0 to 10,000 wt %, preferably 0 to 1,000 wt %, more preferably 100 to 500 wt %, based on the total weight (100 wt %) of the alcohol. An amount exceeding 10,000 wt % is not preferable from the economical viewpoint, since the recovery of the target product becomes cumbersome.

The reaction can proceed without adding a polymerization inhibitor. It is, however, optional to add a polymerization inhibitor in order to make the reaction proceed smoothly while suppressing a polymerization reaction of the acrylic ester compound (reaction product). A polymerization inhibitor can be used without particular limitation as long as it captures radicals. Preferable examples of the polymerization inhibitor include hydroquinone, methoquinone, 2,5-di-t-butylhydroquinone, 2,6-di-t-butylhydroquinone, 2,2'-methylene-bis(4-methyl-6-t-butylphenol), and phenothiazine. The polymerization inhibitor may be in the form of a single compound or a mixture of at least two compounds.

The amount of the polymerization inhibitor may be 0 to 20 wt %, preferably 0.01 to 10 wt %, more preferably 0.1 to 5 wt %, based on the total weight (100 wt %) of the alcohol.

The reaction temperature may be from −50° C. to +300° C., preferably −10° C. to +200° C., more preferably +50° C. to +150° C.

The reaction vessel may be made of a resin material (e.g., ethylene tetrafluoride resin, chlorotrifluoroethylene resin, vinylidene fluoride resin, and PFA resin). It may be one lined with glass or the like. Furthermore, it may be a glass vessel or stainless steel vessel.

For example, it is possible to conduct the reaction by mixing together the alcohol represented by the formula (1), a solvent and an alkene in a reaction vessel that is proof against the reaction condition, followed by adding the acid halide represented by the formula (2) into the reaction system. The reaction end point can be found by sampling or the like.

It is possible to use a conventional purification process for purifying the acrylic ester produced by the process of the invention. For example, the reaction liquid is treated with water, alkali water, brine or the like to remove an excess of the acid halide. The resulting crude organic matter can be purified by column chromatography or distillation.

The following nonlimiting examples are illustrative of the present invention.

EXAMPLE 1

Synthesis of Acrylic Ester Represented by Formula (3)

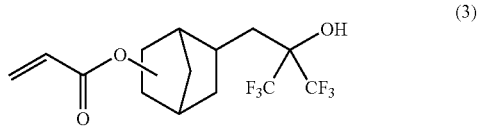

(3)

A 10-liter, four-necked flask equipped with a reflux condenser was charged with 7 liter of toluene, 1,400 g of an alcohol represented by the formula (1) wherein $R^1$ was a hydrogen atom, and 673 g of 2-methyl-2-butene, followed by stirring. Then, 521 g of acrylic chloride were gradually added in a dropwise manner. While the flask was immersed in an oil bath, the reaction liquid was heated to 90° C. by increasing the oil bath temperature. 7 hr later, the reaction liquid composition was analyzed by gas chromatography. With this, it was found that an isomeric mixture represented by the formula (3) was obtained with a conversion of 95%. As impurities, there were obtained 1.4% of the raw material and 0.9% of a chlorine adduct formed by the addition of hydrochloric acid to the unsaturated bond of the acrylic ester of the formula (3). After the reaction liquid was cooled down by standing still under room temperature, saturated brine was added in a dropwise manner. The obtained aqueous layer was separated from the organic layer, followed by extraction of the aqueous layer with toluene three times. The resulting extract and the organic layer were combined together, followed by washing with saturated brine. After drying with anhydrous magnesium sulfate, the solvent was distilled off, thereby obtaining 1728 g of a crude organic matter. Then, this crude organic matter was purified by distillation under reduced pressure, thereby obtaining 1205 g of the acrylic ester of the formula (3). The obtained product was analyzed by gas chromatography. With this, the total conversion of the target product was found to be 95.8%, and the raw material and the chlorine adduct were found to be in 1.8% and 0.4%, respectively. The target isomeric mixture of the formula (3) was recovered without loss during the purification conducted after the reaction.

The identification data of the product were as follows.

$^1$H NMR (CDCl$_3$, TMS standard, 400 MHz) δ 0.77–2.32 (m, 11H), 3.74–3.94 (m, 1H), 4.62 (d, J=5.6 Hz, 1H), 5.82 (d, J=10.4, 1H), 6.80 (dd, J=17.4, 10.4, 1H), 6.37 (d, J=17.4, 1H)

$^{19}$F NMR (CDCl$_3$, CFCl$_3$ standard, 376 MHz) δ–77.0 (q, J=9.2 Hz, 3F), –77.7 (q, J=9.2 Hz, 3F)

EXAMPLE 2

Synthesis of Methacrylic Ester Represented by Formula (4)

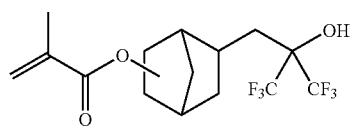

(4)

A 50 mL, three-necked flask equipped with a reflux condenser was charged with 6 mL of toluene, 1151 mg of an alcohol represented by the formula (1) wherein R$^1$ was a hydrogen atom, and 577 mg of 2-methyl-2-butene, followed by stirring. Then, 516 mg of methacrylic chloride were gradually added in a dropwise manner. While the flask was immersed in an oil bath, the reaction liquid was heated to 90° C. by increasing the oil bath temperature. 7 hr later, the reaction liquid composition was analyzed by gas chromatography. With this, it was found that an isomeric mixture represented by the formula (4) was obtained with a conversion of 93%. As impurities, there were obtained 3% of the raw material and 1% of a chlorine adduct formed by the addition of hydrochloric acid to the unsaturated bond of the acrylic ester of the formula (4). After the reaction liquid was cooled down by standing still under room temperature, saturated brine was added in a dropwise manner. The obtained aqueous layer was separated from the organic layer, followed by extraction of the aqueous layer with toluene three times. The resulting extract and the organic layer were combined together, followed by washing with saturated brine. After drying with anhydrous magnesium sulfate, the solvent was distilled off, thereby obtaining 1582 mg of a crude organic matter. Then, this crude organic matter was purified by a thin layer chromatography (hexane/ethyl acetate=5/1), thereby obtaining 1087 mg of the methacrylic ester of the formula (4). The obtained product was analyzed by gas chromatography. With this, the total conversion of the target product was found to be 96%, and the raw material was found to be in 1%. The target isomeric mixture of the formula (4) was recovered without loss during the purification conducted after the reaction.

The identification data of the product were as follows.

$^1$H NMR (CDCl$_3$, TMS standard, 400 MHz) δ 0.63–2.37 (m, 14H), 3.08–3.47 (m, 1H), 4.61–4.66 (m, 1H), 5.54 (s, 1H), 6.06 (s, 1H), 6.37 (s, 1H)

$^{19}$F NMR (CDCl$_3$, CFCl$_3$ standard, 376 MHz) δ–77.1–– 77.8 (m, 6F)

EXAMPLE 3

Synthesis of 2-Trifluoromethylacrylic Ester Represented by Formula (5)

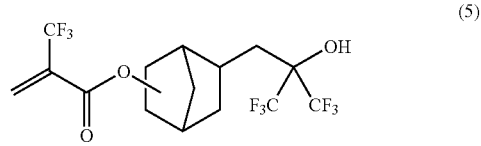

(5)

A 50 mL, three-necked flask equipped with a reflux condenser was charged with 5 mL of toluene, 1010 mg of an alcohol represented by the formula (1) wherein R$^1$ was a hydrogen atom, and 504 mg of 2-methyl-2-butene, followed by stirring. Then, 683 mg of trifluoromethacrylic chloride were gradually added in a dropwise manner. While the flask was immersed in an oil bath, the reaction liquid was heated to 90° C. by increasing the oil bath temperature. 6 hr later, the reaction liquid composition was analyzed by gas chromatography. With this, it was found that an isomeric mixture represented by the formula (5) was obtained with a conversion of 77%. As impurities, there were obtained 14% of the raw material and 5% of a chlorine adduct formed by the addition of hydrochloric acid to the unsaturated bond of the acrylic ester of the formula (5). After the reaction liquid was cooled down by standing still under room temperature, saturated brine was added in a dropwise manner. The obtained aqueous layer was separated from the organic layer, followed by extraction of the aqueous layer with toluene three times. The resulting extract and the organic layer were combined together, followed by washing with saturated brine. After drying with anhydrous magnesium sulfate, the solvent was distilled off, thereby obtaining 1725 mg of a crude organic matter. Then, this crude organic matter was purified by a thin layer chromatography (hexane/ethyl acetate=3/1), followed by recrystallization from hexane, thereby obtaining 387 mg of the 2-trifluoromethylacrylic ester of the formula (5). The obtained product was analyzed by gas chromatography. With this, the total conversion of the target product was found to be 98%. Thus, the target isomeric mixture of the formula (4) was recovered without loss during the purification conducted after the reaction.

The identification data of the product were as follows.

$^1$H NMR (CDCl$_3$, TMS standard, 400 MHz) δ 0.68–2.41 (m, 11H), 2.92–3.10 (m, 1H), 4.72–4.78 (m, 1H), 6.40 (s, 1H), 6.69 (s, 1H)
$^{19}$F NMR (CDCl$_3$, CFCl$_3$ standard) δ −66.1 (s, 3F), −77.1––78.0 (m, 6F)

COMPARATIVE EXAMPLE 1

Synthesis of Acrylic Ester Represented by Formula (3) under Basic Condition

A 100 mL, three-necked flask equipped with a reflux condenser was charged with 20 mL of THF, 3.1 g of an alcohol represented by the formula (1) wherein R$^1$ was a hydrogen atom, and 1.2 g of 2,6-lutidine, followed by stirring. Then, 1.2 g of acrylic chloride were gradually added in a dropwise manner. The reaction liquid was heated at 70° C. with an oil bath under reflux. 3 hr later, the reaction liquid composition was analyzed by gas chromatography. With this, it was found that an isomeric mixture represented by the formula (3) was obtained with a conversion of 94%. As impurities, there were obtained 1% of a cyclized substituted norbornene and 2% of the raw material. After the reaction liquid was cooled down by standing still under room temperature, 10 mL of toluene were added. The resulting salt was filtered out. The obtained filtrate was washed with 5% hydrochloric acid aqueous solution. After distilling the solvent out, 13 mL of toluene were added to the obtained crude reaction liquid, followed by washing with 13 mL of 10% hydrochloric acid aqueous solution. After drying with anhydrous magnesium sulfate, the solvent of the obtained organic layer was distilled out, thereby obtaining 2.0 g of a crude organic matter. Recovery of the target product of the formula (3) was found to be 55%.

COMPARATIVE EXAMPLE 2

Synthesis of Acrylic Ester Represented by Formula (3) without Alkene

A 100 mL, three-necked flask equipped with a reflux condenser was charged with 18 mL of toluene, and 3.5 g of an alcohol represented by the formula (1) wherein R$^1$ was a hydrogen atom, followed by stirring. Then, 1.6 g of acrylic chloride were gradually added in a dropwise manner. While the flask was immersed in an oil bath, the reaction liquid was heated to 70° C. by increasing the oil bath temperature. 3 hr later, the reaction liquid composition was analyzed by gas chromatography. With this, it was found that an isomeric mixture represented by the formula (3) was obtained with a conversion of 77%. As impurities, there were obtained 7% of the raw material and 11% of a chlorine adduct formed by the addition of hydrochloric acid to the unsaturated bond of the acrylic ester of the formula (3). After the reaction liquid was cooled down by standing still under room temperature, saturated brine was added in a dropwise manner. The obtained aqueous layer was separated from the organic layer, followed by extraction of the aqueous layer with toluene three times. The resulting extract and the organic layer were combined together, followed by washing with saturated brine. After drying with anhydrous magnesium sulfate, the solvent was distilled off, thereby obtaining 4.4 g of a crude organic matter. The target isomeric mixture of the formula (3) was recovered without loss during the purification conducted after the reaction.

Differences among Example 1 and Comparative Examples 1 and 2 are summarized in the following table.

TABLE

|  | Com. Ex. 1 | Com. Ex. 2 | Example 1 |
|---|---|---|---|
| Additive | 2,6-lutidine | None | 2-methyl-2-butene |
| Reaction Temperature (° C.) | 70 | 70 | 90 |
| Reaction Time (hr) | 3 | 3 | 7 |
| GC selectivity (%) |  |  |  |
| Raw Material | 2 | 7 | 1 |
| Target Ester of Formula (3) | 94 | 77 | 95 |
| HCl Adduct | Not Found | 11 | 1 |
| Product Recovery after Distilling Solvent out (%) | 55 | Total Amount (100) | Total Amount (100) |

The contents of Table are discussed as follows. In Comparative Example 1 where 2,6-lutidine was used as a base, the target ester of the formula (3) was high in GC selectivity. Its recovery, however, was very low (55%), since the target ester of the formula (3) was incorporated into 2,6-lutidine hydrochloride during the washing step. In Comparative Example 2, it was possible to recover the target ester of the formula (3) without loss during the washing step. However, a high amount (11%) of the hydrochloric acid adduct was formed during the reaction. As a result, the target ester of the formula (3) became low in GC selectivity. In Example 1 where an alkene was used, it was possible to suppress the formation of the hydrochloric acid adduct during the reaction to 1%, and it was possible to recover the target ester of the formula (3) without loss during the washing step. As a result, it was possible to obtain the target ester with a high yield of not lower than 80%.

What is claimed is:

1. A process for producing an acrylic ester compound, comprising reacting in the presence of an alkene an alcohol represented by the formula (1),

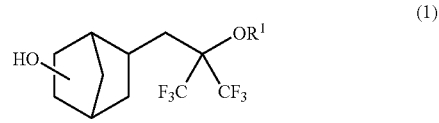
(1)

wherein R$^1$ represents a hydrogen atom, a fluorine atom, a straight-chain or branched hydrocarbon group, a fluorine-containing alkyl group, or an aromatic or aliphatic ring and optionally contains oxygen, sulfur or a carbonyl bond, with an acid halide represented by the formula (2),

(2)

wherein R$^2$ represents a hydrogen atom, a halogen atom, a hydrocarbon group, or a fluorine-containing alkyl group, and X represents a halogen atom.

2. A process according to claim 1, wherein R$^1$ of the formula (1) represents a hydrogen atom.

3. A process according to claim 1, wherein $R^1$ of the formula (1) represents (a) a hydrocarbon group selected from the group consisting of methyl group, ethyl group, isopropyl group, cyclopropyl group, cyclopentyl group, cyclohexyl group, norbornel group, adamantyl group, and benzyl group; (b) an acyclic or cyclic ether; (c) an aromatic ring that is 4-methoxybenzyl group; or (d) a carbonyl-containing group selected from the group consisting of acetyl group, pivaloyl group, tert-butoxycarbonyl group, and benzoyl group.

4. A process according to claim 3, wherein the acyclic ether is methoxymethyl ether or methoxyethoxymethyl ether, and the cyclic ether is tetrahydrofuran or tetrahydropyran.

5. A process according to claim 1, wherein $R^2$ of the formula (2) represents a hydrogen atom, a fluorine atom, a methyl group, a trifluoromethyl group, a $C_1$–$C_4$ straight-chain or branched hydrocarbon group, or a $C_1$–$C_4$ straight-chain or branched fluorine-containing alkyl group.

6. A process according to claim 1, wherein X of the formula (2) represents a chlorine, bromine or iodine atom.

7. A process according to claim 6, wherein X of the formula (2) represents a chlorine atom.

8. A process according to claim 1, wherein the acid halide is in an amount of 1 to 5 equivalents per equivalent of the alcohol.

9. A process according to claim 1, wherein the alkene is not a conjugated diene.

10. A process according to claim 1, wherein the alkene is at least one selected from the group consisting of isobutene, 2-methyl-2-butene, 2-methyl-2-pentene, 1-methyl-1-cyclopentene, cyclohexene, 1-methyl-1-cyclohexene, methylenecyclohexane, and norbornene.

11. A process according to claim 1, wherein the alkene is in an amount of 0.1 to 50 equivalents per equivalent of the alcohol.

12. A process according to claim 1, wherein the reaction is conducted in the presence of a polymerization inhibitor.

13. A process according to claim 12, wherein the polymerization inhibitor is at least one selected from the group consisting of hydroquinone, methoquinone, 2,5-di-t-butylhydroquinone, 2,6-di-t-butylhydroquinone, 2,2'-methylene-bis(4-methyl-6-t-buthylphenol), and phenothiazine.

14. A process according to claim 12, wherein the polymerization inhibitor is in an amount of not greater than 20 wt %, based on an amount of the alcohol.

15. A process according to claim 1, wherein the reaction is conducted at a temperature of 50° C. to 150° C.

* * * * *